US011511035B2

United States Patent
Abrams et al.

(10) Patent No.: US 11,511,035 B2
(45) Date of Patent: Nov. 29, 2022

(54) IMPLANTABLE INTRAVENTRICULAR SAMPLING AND INFUSION ACCESS DEVICE

(71) Applicant: Cerebral Therapeutics, Inc., Aurora, CO (US)

(72) Inventors: Daniel J. Abrams, Denver, CO (US); Michael S. Canney, Denver, CO (US)

(73) Assignee: CEREBRAL THERAPEUTICS, INC., Aurora, CO (US)

( * ) Notice: Subject to any disclaimer, the term of this patent is extended or adjusted under 35 U.S.C. 154(b) by 280 days.

(21) Appl. No.: 15/663,095

(22) Filed: Jul. 28, 2017

(65) Prior Publication Data

US 2018/0028746 A1     Feb. 1, 2018

Related U.S. Application Data

(60) Provisional application No. 62/367,713, filed on Jul. 28, 2016.

(51) Int. Cl.
*A61M 5/142*     (2006.01)
*A61M 25/00*     (2006.01)
(Continued)

(52) U.S. Cl.
CPC ..... *A61M 5/14276* (2013.01); *A61B 10/0045* (2013.01); *A61M 5/16831* (2013.01);
(Continued)

(58) Field of Classification Search
CPC .......... A61M 39/0208; A61M 39/0247; A61M 39/02; A61M 27/002; A61M 27/006;
(Continued)

(56) References Cited

U.S. PATENT DOCUMENTS 3,640,269 A * 2/1972 Delgado ........... A61M 39/0208
                                                        600/573
4,464,168 A * 8/1984 Redmond ........... A61M 27/006
                                                        604/9
(Continued)

FOREIGN PATENT DOCUMENTS

WO         9427587 A2     12/1994
WO     2008115919 A2     9/2008
(Continued)

OTHER PUBLICATIONS

NPL01_International Search Report and Written Opinion for PCT/US2017/044452 dated Nov. 2, 2017. pp. 15.
(Continued)

*Primary Examiner* — Kami A Bosworth
*Assistant Examiner* — Alexandra Lalonde
(74) *Attorney, Agent, or Firm* — Mueting Raasch Group (57) ABSTRACT

In some embodiments, a device may include an intraventricular access device and an infusion device. The intraventricular access device may include more than one catheter and a container. In some embodiments, the catheter may include an aspiration lumen and an infusion lumen. A distal end of the intraventricular portion of the catheter may be positionable, during use, in a subject's brain fluid. In some embodiments, the container may be coupled to a proximal end of the aspiration lumen. The proximal end of the aspiration lumen may be in fluid communication with the container. In some embodiments, the container may include a barrier positioned between a proximal opening of the aspiration lumen and at least a portion of the infusion lumen adjacent to and/or associated with the container. The barrier may inhibit penetration of a surgical instrument.

23 Claims, 9 Drawing Sheets

(51) Int. Cl.
- A61B 10/00 (2006.01)
- A61M 39/02 (2006.01)
- A61M 5/168 (2006.01)
- A61M 5/14 (2006.01)

(52) U.S. Cl.
CPC .......... *A61M 25/003* (2013.01); *A61M 39/02* (2013.01); *A61M 39/0208* (2013.01); *A61B 2010/0077* (2013.01); *A61M 2005/1406* (2013.01); *A61M 2025/0031* (2013.01); *A61M 2210/0693* (2013.01)

(58) Field of Classification Search
CPC .. A61M 2210/0693; A61M 2210/0687; A61M 2025/0037; A61M 2025/0031; A61M 25/007; A61M 25/0026; A61M 25/003; A61M 25/0015; A61M 2027/004; A61M 3/0283; A61M 5/14276; A61M 2039/0214; A61M 2039/0211; A61M 2039/0226; A61M 2039/0202; A61M 2039/0205; A61M 2039/0217; A61M 2039/022; A61M 2039/0223; A61M 2039/0229; A61M 2039/0232; A61M 2039/0235; A61M 2039/0238; A61M 2039/0241; A61M 2039/0244; A61M 2005/1406; A61M 5/16831; A61B 5/6868

See application file for complete search history.

(56) References Cited

U.S. PATENT DOCUMENTS

| | | | |
|---|---|---|---|
| 4,723,556 A | 2/1988 | Sussman | |
| 4,767,410 A * | 8/1988 | Moden | A61M 39/0208 604/175 |
| 4,904,241 A * | 2/1990 | Bark | A61M 39/0208 604/117 |
| 5,522,807 A * | 6/1996 | Luther | A61M 25/0068 604/523 |
| 5,720,720 A * | 2/1998 | Laske | A61M 25/0075 604/21 |
| 5,810,789 A | 9/1998 | Powers et al. | |
| 6,013,051 A * | 1/2000 | Nelson | A61M 39/0208 604/247 |
| 6,293,922 B1 * | 9/2001 | Haase | A61M 39/0208 604/93.01 |
| 7,670,327 B2 | 3/2010 | Kucharczyk et al. | |
| 8,277,425 B2 | 10/2012 | Girard et al. | |
| 8,808,234 B2 | 8/2014 | Vogelbaum et al. | |
| 8,979,822 B2 | 3/2015 | Vogelbaum et al. | |
| 2003/0135148 A1 * | 7/2003 | Dextradeur | A61M 25/0662 604/8 |
| 2004/0002677 A1 * | 1/2004 | Gentsler | A61B 17/12045 604/22 |
| 2004/0073196 A1 | 4/2004 | Adams et al. | |
| 2004/0171983 A1 | 9/2004 | Sparks et al. | |
| 2005/0004219 A1 * | 1/2005 | Hildebrand | A61M 5/14276 514/561 |
| 2005/0038371 A1 | 2/2005 | Reich et al. | |
| 2005/0070458 A1 * | 3/2005 | John | A61B 5/031 514/1 |
| 2005/0137578 A1 | 6/2005 | Heruth et al. | |
| 2005/0209332 A1 | 9/2005 | Kuppuswamy et al. | |
| 2006/0160889 A1 | 7/2006 | Hildebran et al. | |
| 2007/0083063 A1 | 4/2007 | Nelson et al. | |
| 2008/0039774 A1 * | 2/2008 | Zawacki | A61M 25/0026 604/43 |
| 2008/0262374 A1 * | 10/2008 | Gerber | A61M 5/16836 600/547 |
| 2009/0131850 A1 * | 5/2009 | Geiger | A61M 27/006 604/9 |
| 2009/0131857 A1 * | 5/2009 | Geiger | A61K 31/145 604/28 |
| 2010/0158869 A1 * | 6/2010 | Kaemmerer | C12N 15/111 424/93.6 |
| 2010/0286585 A1 * | 11/2010 | DiMauro | A61K 31/12 604/8 |
| 2010/0305492 A1 | 12/2010 | Lad et al. | |
| 2011/0033463 A1 | 2/2011 | Thakker et al. | |
| 2011/0092921 A1 * | 4/2011 | Beling | G09F 23/00 604/288.02 |
| 2011/0172633 A1 * | 7/2011 | Ali | A61M 5/14276 604/500 |
| 2011/0275930 A1 * | 11/2011 | Jho | A61B 5/064 600/424 |
| 2012/0087869 A1 | 4/2012 | Thakker et al. | |
| 2012/0310140 A1 | 12/2012 | Kramer et al. | |
| 2013/0253266 A1 * | 9/2013 | Dextradeur | A61M 25/0068 600/104 |
| 2014/0257168 A1 * | 9/2014 | Gill | A61M 27/006 604/9 |
| 2015/0238685 A1 * | 8/2015 | Elias | A61N 1/36139 600/420 |
| 2015/0297874 A1 * | 10/2015 | East | A61M 27/006 604/9 |
| 2016/0122282 A1 | 5/2016 | Kandula | |
| 2016/0374901 A9 | 12/2016 | Rodriguez et al. | |

FOREIGN PATENT DOCUMENTS

| | | |
|---|---|---|
| WO | 2009014762 A1 | 1/2009 |
| WO | 2009151741 A1 | 12/2009 |
| WO | 2018023041 A1 | 2/2018 |
| WO | 2019084038 A1 | 5/2019 |

OTHER PUBLICATIONS

Abrams "Feasibility of Delivery of Anti-Epilepsy Medications into the Cerebrospinal Fluid (10802)" Neuromodulation, vol. 19, No. 3, p. e107, Dec. 10, 2015.

Barcia et al. "Intraventricular and Intracerebral Delivery of Antiepileptic Drugs in the Kindling Model", vol. 6, No. 2, pp. 337-343, Apr. 1, 2009.

International Search Report and Written Opinion for PCT/US2019/068592 dated Apr. 24, 2020, 12 pages.

Serralta et al. "Effect of intracerebroventricular continuous infusion of valproic acid versus single i.p. and i.c.v. injections in the amygdala kindling epilepsy model", vol. 70, No. 1, pp. 15-26 Jul. 1, 2006.

International Preliminary Report on Patentability for PCT/US2019/068592 dated Jul. 29, 2021, 9 pages.

\* cited by examiner

IMPLANTABLE INTRAVENTRICULAR SAMPLING AND INFUSION ACCESS DEVICE

PRIORITY CLAIM

This application claims priority to U.S. Provisional Application Ser. No. 62/367,713 entitled "IMPLANTABLE INTRAVENTRICULAR SAMPLING AND INFUSION ACCESS DEVICE" filed on Jul. 28, 2016, which is incorporated herein by reference in its entirety.

BACKGROUND OF THE INVENTION

1. Field of the Invention

The present disclosure generally relates to intraventricular administration of drugs to the brain. More particularly, the disclosure generally relates to an intraventricular access device configurable to provide continuous drug infusion and/or access for sampling of cerebrospinal fluid.

2. Description of the Relevant Art

One of the principle reasons for directly administering drug therapies to the brain is due to the blood-brain barrier (BBB). The BBB limits that passage of nearly all large molecule and the majority of small molecule drugs (<500 Da) to the brain parenchyma. Since the BBB limits the penetration of drugs from the vasculature to the brain tissue, most drugs that are administered orally or by intravenous infusion do not reach sufficient concentrations in the brain parenchyma to have therapeutic effects. In addition, drugs that may have the highest potential efficacy against cancerous tissue are unable to reach the target tissue. For example, trastuzumab, a humanized IgG1 kappa monoclonal antibody for the treatment of metastatic breast cancer has a cerebrospinal fluid (CSF) level that is 300-fold lower than plasma levels when administered intravenously.

Several methods have been proposed to bypass the BBB to increase drug concentrations in the brain. These include methods for altering the administration of drugs for brain delivery including: convection-enhanced delivery (CED), intra-arterial injection, high dose systemic chemotherapy, drug-loaded wafers that are inserted directly into the tumor resection cavity, and administration of drugs to the CSF.

Methods also exist to temporarily increase the permeability of the BBB and include the use of osmotic solutions (mannitol), pulsed ultrasound in combination with microbubbles, and radiation therapy.

One method for direct administration of drugs to bypass the BBB is the use of an ommaya reservoir, which is described below. The Ommaya Reservoir is a type of device that allows for direct access to the CSF from a syringe or external pump without additional surgery at each drug administration. An external ventricular drain is another type of device that allows for access to the CSF, typically to drain excess CSF to relieve and reduce intracranial pressure (ICP).

The Ommaya Reservoir is an intraventricular catheter system that allows for either sampling of cerebrospinal fluid or less commonly intermittent direct administration of drugs to the CSF. They were invented in 1963 and when used for chemotherapy are primarily used for the delivery of chemotherapy agents such as methotrexate or Ara-C to the CSF for patients with leptomeningeal disease and for continuous sampling of the CSF for potential infection, progression of CSF based cancers and occasionally for obtaining a drug level. One example of such a reservoir is the Integra™ Reservoir (Integra LifeSciences Corporation).

Several types of external ventricular drains exist to provide access to the CSF. These types of catheters are classified as Class 2 medical devices by the FDA. They may have an antibacterial coating to limit infection, which can occur in up to 25% of catheter placements in the brain. For example, the Ares™ Antibiotic Impregnated Catheter (Medtronic) and Bactiseal® (Codman Neuro, DePuySynthes, Johnson & Johnson) are impregnated with rifampicin and clindamycin and prevent bacterial colonization on all surfaces for up to 28 days. Other antibiotics such as minocycline/rifampin or silver may also be used to coat the device to limit infection. They may also contain barium impregnation for visualization on X-ray to verify proper positioning of the device within the brain.

Drug Infusion into the lumbar spine CSF via implantable catheters exist. These catheters infuse drug into a small space with small flow volumes which is because the space required for infusion is small. The size of the holes tends to be small.

In terms of brain catheters currently used for drainage, an example is the Ares™ (Medtronic) ventricular catheter has 32 flow holes with four lines of 8 holes spaced at 90° intervals—to limit clogging from ventricular contents though never a focus on brain drug delivery. These devices are never used for chronic brain drug delivery.

Catheters designed for convection enhanced delivery (CED) have been developed. CED catheters are designed to infuse drug directly into the targeted tissue. The barium-impregnated Medtronic® PS Medical (Goleta, Calif., USA; Catalog number 43209) and Vygon US LLC (Valley Forge, Pa., USA) are examples of devices that have been used in CED trials (Debinski and Tatter 2009). Infuseon Therapeutics (U.S. Pat. Nos. 8,808,234 and 8,979,822 which are incorporated by reference herein) is also developing a new catheter design for CED that allows for delivery of drugs to the brain via four independent flexible micro catheters. The device is designed for use over up to several days (but not for chronic use over weeks or months). The catheters are made from silicon and each microcatheter has a diameter of 0.38 mm. The main issue with CED catheters is backflow of the infusate during infusion and the lack of ability to use them for chronic infusion.

There are known complications beyond intracranial hemorrhage of brain drains which are external to the body and placed most commonly in cases of brain trauma, subarachnoid hemorrhage or post neurosurgical. Infection is one of the most common types of complications associated with such devices. A common practice aimed at reducing this is to administer intravenous antibiotics to cover common skin flora for the duration of EVD placement. Though this appears to carry some benefit, it may contribute to the development of resistant organisms. Antibiotic-impregnated and ionized silver particle coated EVD catheters offer a similar level of protection compared with prophylactic intravenous antibiotics but come at a cost. Other strategies include sampling an EVD only when infection is suspected, monitoring EVD dressing site for drainage suggestive of CSF leak, maintaining collection system in the upright position, and not routinely changing drain tubing. In the setting of infection, it is common consensus that the colonized EVD catheter be removed and replaced with a new catheter, preferentially at a new site. Minimizing infection is a requirement for longer term placement.

The present invention relates to the direct administration of drug therapies to the brain through an intraventricular access device that allows for access to the CSF through a port located just beneath the scalp of a patient. The system can furthermore be attached to an implantable drug pump (e.g. Prometra® Programmable Pump by Flowonix Medical or the Synchromed® by Medtronic) or an external syringe or equivalent type pump.

Accordingly, there is a desire to provide a device for the direct administration of drug therapies to the brain through an intraventricular access device that allows for access to the CSF through a port located just beneath the scalp of a patient.

SUMMARY

In some embodiments, a device may include an intraventricular access device. The intraventricular access device may include a catheter and a container. In some embodiments, the catheter may include an aspiration lumen and an infusion lumen. A distal end of the catheter may be positionable, during use, in a subject's brain. In some embodiments, the container may be coupled to a proximal end of the aspiration lumen. The proximal end of the aspiration lumen may be in fluid communication with the container. In some embodiments, the device inhibits cross contamination between a first fluid in the aspiration lumen and a second fluid in the infusion lumen. In some embodiments, the container may include a barrier positioned between a proximal opening of the aspiration lumen and at least a portion of the infusion lumen adjacent to and/or associated with the container. The barrier may inhibit penetration of a surgical instrument. The container may include a marker to indicate a position of the barrier.

In some embodiments, at least a portion of the infusion lumen is positioned in the aspiration lumen or at least a portion of the aspiration lumen is positioned in the infusion lumen. In some embodiments, the aspiration lumen and the infusion lumen may include two different lumens positioned adjacent one another.

In some embodiments, the aspiration lumen and the infusion lumen are different lengths when positioned, during use, in the subject's brain such that a distal end of the aspiration lumen and a distal end of the infusion lumen are positioned a distance away from one another.

In some embodiments, a distal end of the aspiration lumen comprises a first opening and a distal end of the infusion lumen comprises a second opening. The first opening and the second opening may be directed in a substantially opposing directions to inhibit cross contamination of fluids.

In some embodiments, a distal end of the aspiration lumen and/or the infusion lumen comprises at least one opening or a plurality of openings which are inhibited from opening except when pressure is applied to the opening.

In some embodiments, at least a portion of the container is formed from material that is penetrable by a needle (e.g., a hypodermic needle) and substantially reseals after extraction of the needle.

In some embodiments, at least portions of the device are formed from and/or coated in biocompatible materials which inhibit cell adhesion and/or comprises an antimicrobial.

In some embodiments, the infusion lumen may be coupled to a pump positioned externally or internally relative to the subject.

In some embodiments, a method includes aspirating and infusing at least a portion of a subject's brain. The method may include penetrating an upper portion of a container of a device using a needle. The method may include aspirating a first fluid from a first portion of a subject's brain through an aspiration lumen coupled to the container and using the needle. The method may include infusing a second fluid into a second portion of a subject's brain through an infusion lumen coupled to the container and the aspiration lumen. The method may include inhibiting penetration of the infusion lumen by the needle.

In some embodiments, the method may include infusing the second fluid using a pump coupled to the infusion lumen, wherein the pump is positioned externally or internally relative to the subject. The method may include positioning at least a portion of the infusion lumen coupled to a pump subcutaneously.

In some embodiments, the method may include positioning at least a portion of the aspiration and/or the infusion lumen in the subject's brain using a substantially inflexible stylet. The stylet may be positioned in the aspiration lumen by running the stylet through the container. The method may include observing at least a portion of the device during implantation using neuroimaging.

In some embodiments, the method may include inhibiting penetration of the infusion lumen by the needle using a barrier positioned between a proximal opening of the aspiration lumen and at least a portion of the infusion lumen adjacent to and/or associated with the container.

In some embodiments, the method may include inhibiting at least one opening at a distal end of the aspiration lumen and/or the infusion lumen from opening except when pressure is applied to the opening in a first direction. The method may include inhibiting the at least one opening in a second direction from opening even under pressure.

BRIEF DESCRIPTION OF THE DRAWINGS

Advantages of the present invention may become apparent to those skilled in the art with the benefit of the following detailed description of the preferred embodiments and upon reference to the accompanying drawings.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "catheter" as used herein generally refers to medical devices that can be inserted in the body to treat diseases or perform a surgical procedure.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "stylet" as used herein generally refers to a probe, typically a slender probe.

Intraventricular Access Device:

CSF sampling is inherently important both from a safety and efficacy perspective.

From a safety perspective, the ability to both monitor potential infection as well as drug levels is important. From an efficacy perspective, understanding drug levels will be increasingly important to monitor drug treatments. Accordingly, there is a desire to provide a device for the direct administration of drug therapies to the brain through an intraventricular access device that allows for access to the CSF through a port located just beneath the scalp of a patient. The system can furthermore be attached to an implantable drug pump or an external syringe or equivalent type pump.

In some embodiments, an intraventricular access device may provide an implantable drug delivery device that facilitates drug administration as well as sampling in the brain of a human patient. The access for drug sampling may occur at a separate location than the drug infusion to minimize cross contamination. Drug sampling may be performed with a sharp needle and as such the intraventricular access device includes protections such that the needle for sampling will not penetrate the infusion catheter. With such design safeguards, mixing and inaccuracies may be avoided. Both infusion and sampling access points within the brain are done relatively close to each other as such sampling and infusion may be accomplished in such a way to minimize cross contamination. The drug delivery device is adapted for implantation into a human subject and drug delivery to the CSF. The drug delivery device includes a support structure that may be accessed via skin puncture to sample the CSF.

Figure 1:
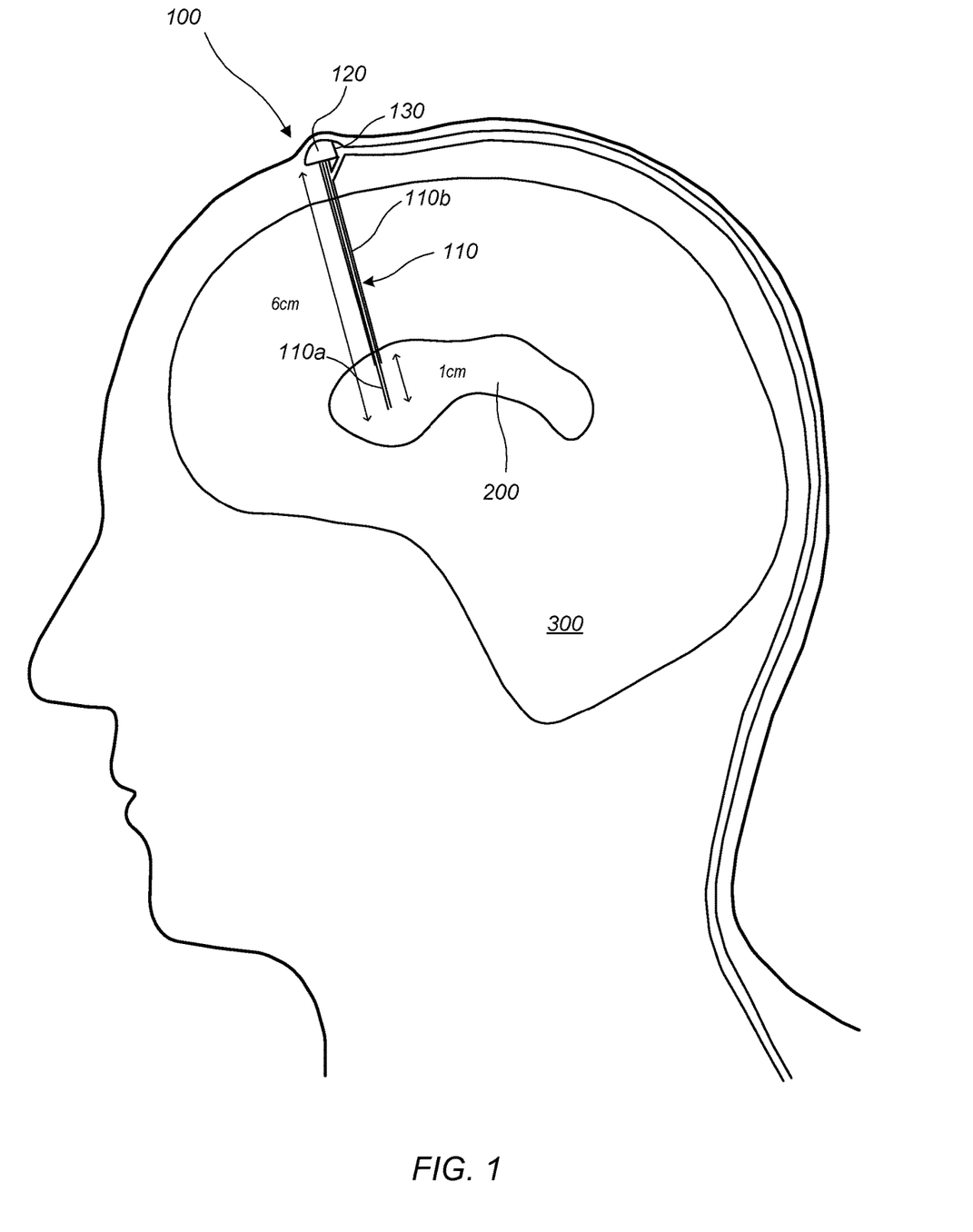
FIG. 1 depicts a diagram of a cross sectional view of an embodiment of a portion of an intraventricular access device, specifically a catheter design with a concentric dual lumen design. Infusion and sampling ports are implanted in one of the lateral ventricles. The infusion port (outer lumen) is connected to an implanted pump.

In some embodiments, a device may include an intraventricular access device 100. FIG. 1 depicts a diagram of a cross sectional view of an embodiment of a portion of an intraventricular access device 100, specifically a catheter design with a concentric dual lumen design. Infusion and sampling ports are implanted in one of the lateral ventricles 200 of a subject's brain 300. The infusion port (outer lumen) is connected to an implanted pump. The intraventricular access device may include a catheter 110 and a container 120. In some embodiments, the catheter may include an aspiration lumen 110a and an infusion lumen 110b. A distal end of the catheter (e.g., 5-6 cm length) may be positionable, during use, in a subject's brain. In some embodiments, the container 120 may be coupled to a proximal end of the aspiration lumen 110a. The proximal end of the aspiration lumen may be in fluid communication with the container. In some embodiments, the device inhibits cross contamination between a first fluid in the aspiration lumen and a second fluid in the infusion lumen. Cross contamination may be inhibited by using two separate lumens for sampling and infusion.

Figure 2:
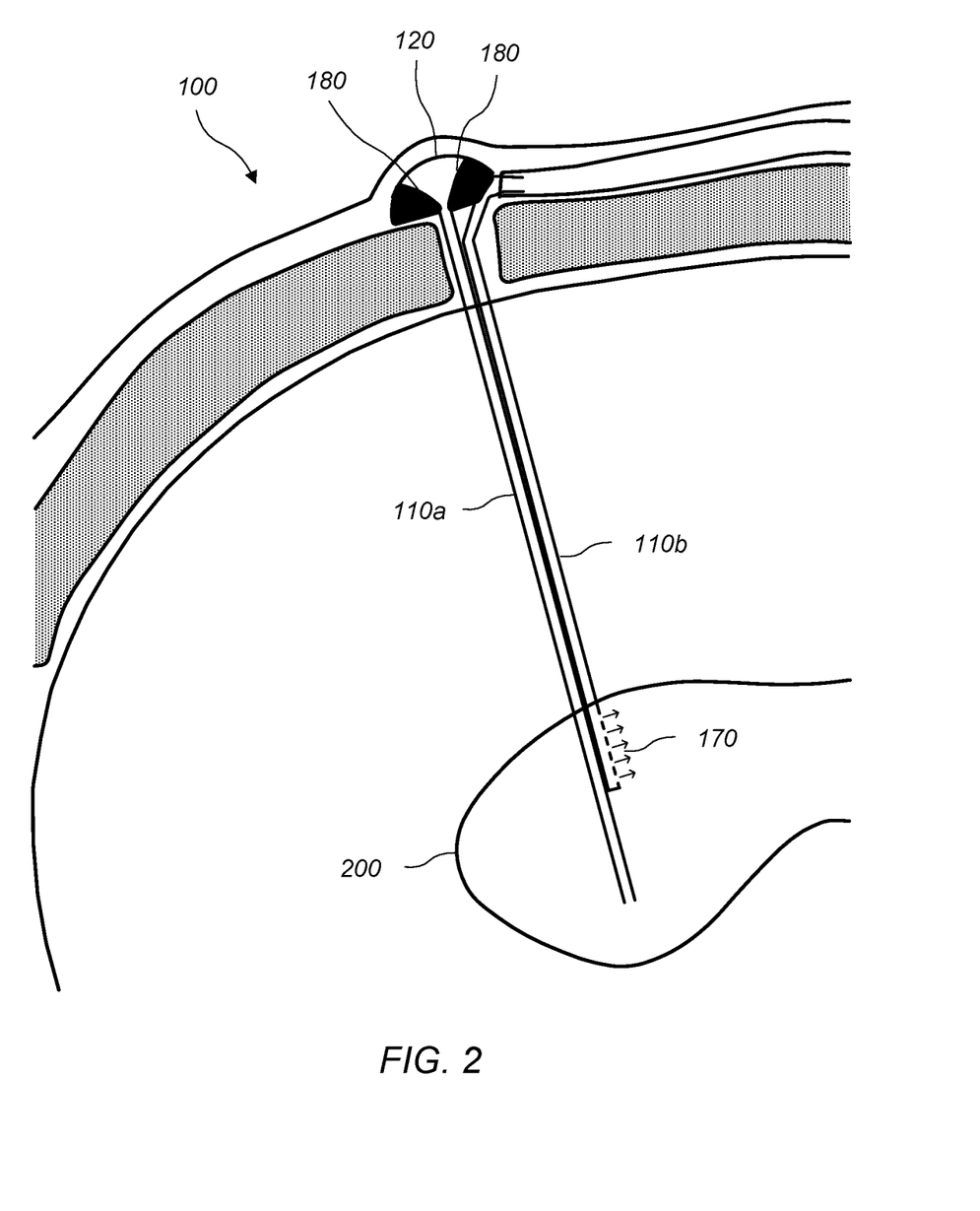
FIG. 2 depicts a diagram of a cross sectional view of an embodiment of a portion of an intraventricular access device, specifically a side by side dual lumen design including an infusion pathway distinct from the infusion catheter coming from the pump which is shielded from the sampling port from being penetrated by a or other needle during aspiration.

Cross contamination may be inhibited using other systems and/or methods. In some embodiments, the container 120 may include a barrier 130 positioned between a proximal opening of the aspiration lumen and at least a portion of the infusion lumen adjacent to and/or associated with the container. The barrier may inhibit penetration of a surgical instrument (e.g., hypodermic needle). For example, a needle may be used to collect a sample from the container conveyed up through the aspiration lumen and the barrier may inhibit accidental puncture of the infusion lumen by the needle during the procedure. FIG. 2 depicts a diagram of a cross sectional view of an embodiment of a portion of an intraventricular access device 100, specifically a side by side dual lumen design including an infusion pathway distinct from the infusion catheter coming from the pump which is shielded from the sampling port from being penetrated by a hypodermic or other needle during aspiration.

In some embodiments, the infusion side or segment and the infusion pathway will be covered by a barrier (e.g., metal or other hard plastic material (e.g. PEEK)) to limit the ability of a needle to penetrate and potentially cause a fenestration between the two sides. The top portion on the container may be a silicon-type material that can be punctured by a needle, but which reseals after the needle is withdrawn. In some embodiments, the container may have guide members 180 (e.g., be a cone-shape) so that the needle will be guided to the location of the sampling lumen 110a.

In some embodiments, the container may include a marker to indicate a position of the barrier. In some embodiments, one or more portions of the intraventricular access device 100 may include a marker of some kind including, but not limited to, any portion of the device positionable within the subject. The device may include multiple individually distinguishable markers. Markers may be used to assess a position of one or more portions of the device during and/or after implantation in a subject. A portion of the implant may include none, one or multiple markers. Markers may provide radiographic opacity. Markers may be biocompatible. Markers may be of any size or shape. In some embodiments, a system may have multiple markers with different shapes in order to more easily identify different portions of the system and/or an orientation of one or more portions of the device. In some embodiments, one or more markers may be formed from gold or tantalum.

Figure 3:
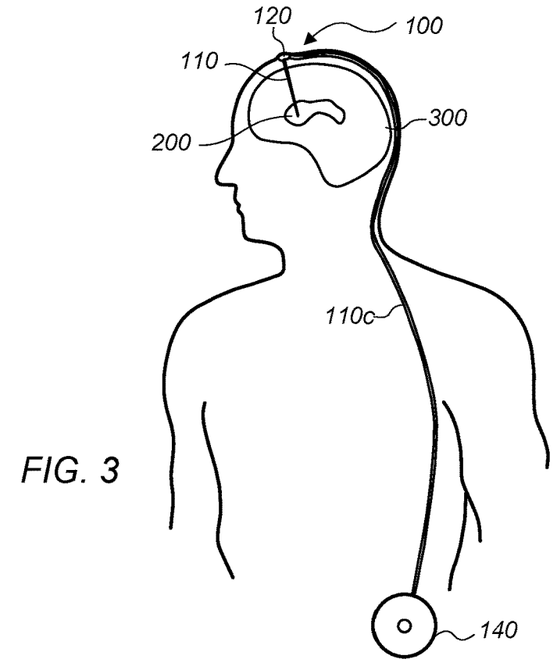
FIG. 3 depicts a diagram of a cross sectional view of an embodiment of an intraventricular access device implanted with the sampling and infusion ports located in one of the lateral ventricles. The infusion and sampling catheter in the brain is connected to a container which is in turn connected to an implantable pump that is located in the abdomen.
Figure 4:
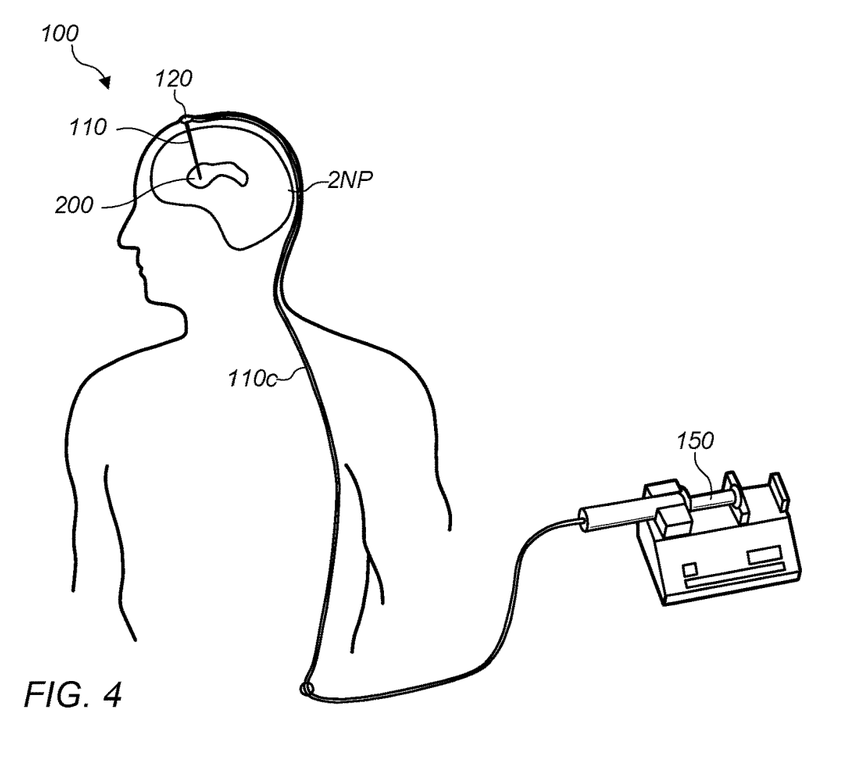
FIG. 4 depicts a diagram of a cross sectional view of an embodiment of an intraventricular access device implanted with the sampling and infusion ports located in one of the lateral ventricles. The infusion and sampling catheter in the brain is connected to a container which is in turn connected to an external syringe pump.

The intraventricular access device may be designed to operate as part of a drug delivery system. The system includes a catheter that has distal openings in the CSF. The proximal side of the catheter is connected to a modified reservoir or container that may be accessed using, for example, a standard needle to draw CSF fluid from the distal end of the catheter to sample the CSF. In some embodiments, the infusion lumen may be coupled to a pump positioned externally or internally relative to the subject. For example, the container may contain a pathway for drug infusion and is connectable to a catheter which may connect to an implantable, programmable, refillable, drug pump. The pump may be implanted in the abdominal region of a patient. FIG. 3 depicts a diagram of a cross sectional view of an embodiment of an intraventricular access device 100 implanted with the sampling and infusion ports 110a-b located in one of the lateral ventricles 200. The infusion and sampling catheter in the brain is connected to a container 120 which is in turn connected to an implantable pump 140 (e.g., via an extension of the infusion lumen or an additional lumen 110c coupled to the infusion lumen) that is located, for example, in the abdomen. In some embodiments, a drug pump may be connected to an external pump 150 in addition to or in the alternative to an implantable pump. FIG. 4 depicts a diagram of a cross sectional view of an embodiment of an intraventricular access device 100 implanted with the sampling and infusion ports 110a-b located in one of the lateral ventricles 200. The infusion and sampling catheter in the brain is connected to a container 120 which is in turn connected to an external pump 150 (e.g., a syringe pump via an extension of the infusion lumen or an additional lumen 110c coupled to the infusion lumen).

In some embodiments, implantable drug pumps such as the Synchromed® (Medtronic) or Prometra® (Flowonix)

may be used for local and continuous infusion of drug therapies. These drug pumps are currently indicated for intrathecal drug delivery and have 20-40 mL refillable reservoirs. They are indicated for the treatment of chronic, intractable pain, severe spasticity, and cancer. Alternatively, an external syringe type pump can be utilized. Syringe type pumps can include a pump like a Baxter 150XL. For other descriptions of potential pumps Medications which may be introduced using the herein described system are not limited. In some embodiments, Morphine and Baclofen are both drugs that could be used as well as chemotherapies and other drugs for treatment of chronic and nonchronic diseases of the brain.

Figure 5:
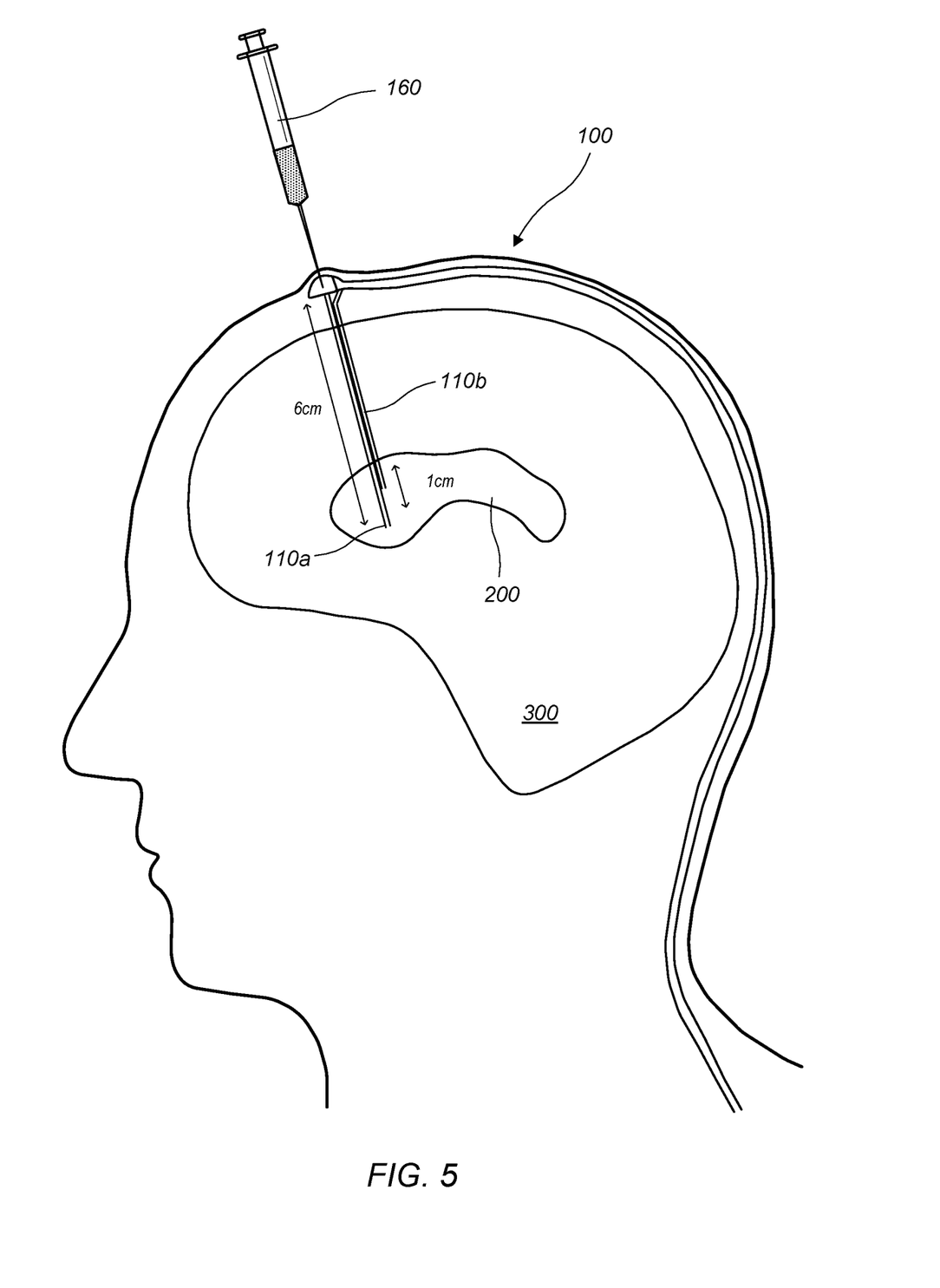
FIG. 5 depicts a diagram of a cross sectional view of an embodiment of a portion of an intraventricular access device, specifically a side by side dual lumen design. The infusion and sampling ports are implanted in one of the lateral ventricles. A container fluidly coupled to at least the infusion lumen may allow either directly inject drugs into the ventricles, or to sample CSF from the patient using an external syringe (or an external pump).

In some embodiments, aspiration lumen 110a may function as a sampling portal for obtaining a sample of a subject's fluid. FIG. 5 depicts a diagram of a cross sectional view of an embodiment of a portion of an intraventricular access device 100, specifically a side by side dual lumen design. The infusion and sampling ports are implanted in one of the lateral ventricles. A container 120 fluidly coupled to at least the infusion lumen 110a may allow either directly inject drugs into the ventricles, or to sample CSF from the patient using an external syringe 160 (or an external pump 150).

Figure 6:
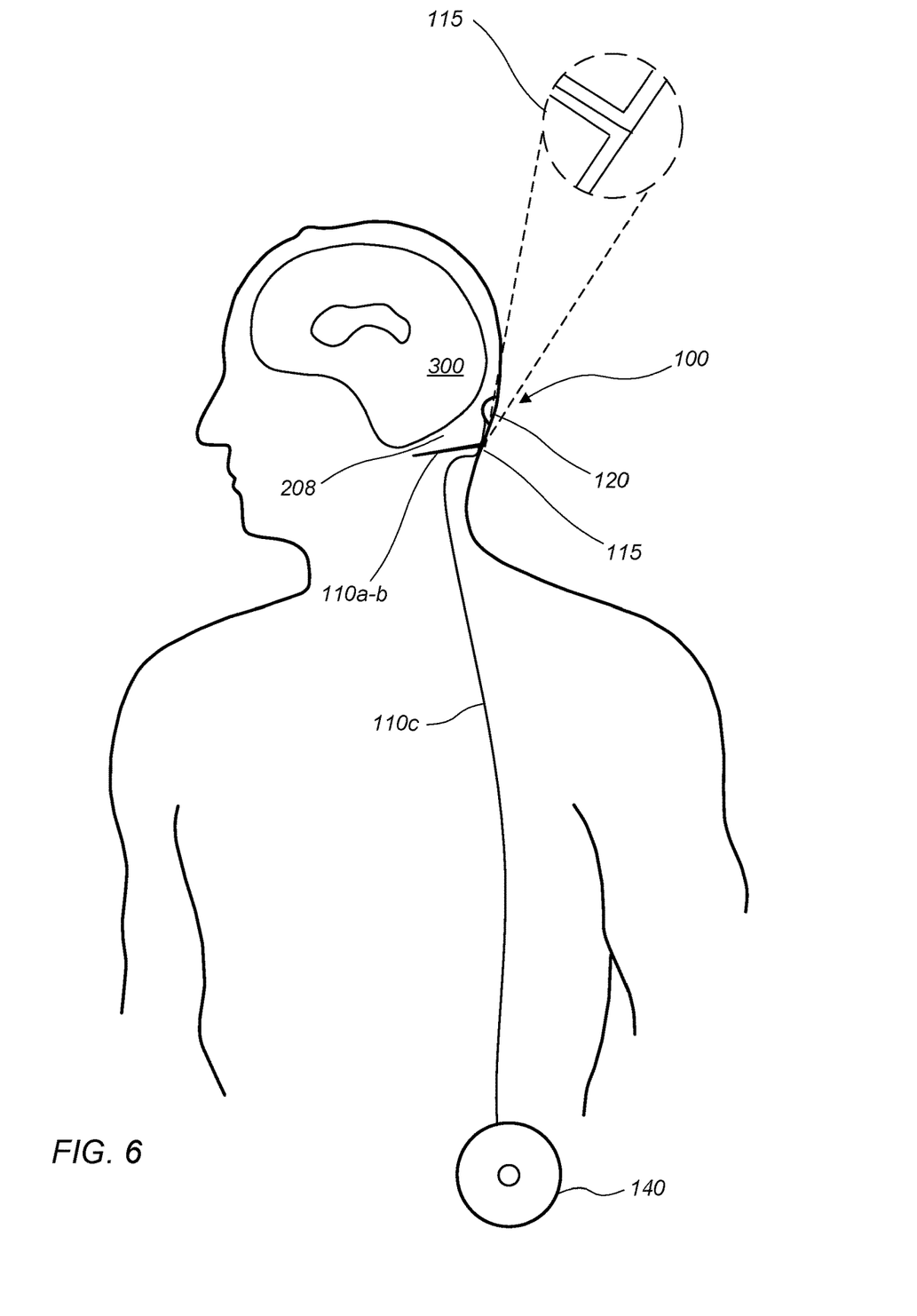
FIG. 6 depicts a diagram of a cross sectional view of an embodiment of an access device implanted with the sampling and infusion ports located over the cisterna magna and the cerebellum. The tip of the catheter can be directed to the cisterna magna, cisterns in the cerebellopontine angle, in the fourth ventricle or in the supra-cerebellar cistern direction. The infusion and sampling catheter in the brain is connected to a container which is in turn connected to an implantable pump that is located in the abdomen.

In some embodiments, in the access device 100 the lumens 110 are tunneled up to the cisterna magna along the spine. FIG. 6 depicts a diagram of a cross sectional view of an embodiment of an access device 100 implanted with the sampling and infusion ports located in the cisterna magna. The infusion and sampling catheter in the brain is connected to a container 120 which is in turn connected to an implantable pump 140 that is located in the abdomen. The lumens 110 inserted into a spinal canal and tunneled (e.g., using a guidewire). In some embodiments, the container 120 (e.g., sampling reservoir) would either sit above the occipital bone, or the muscle layer of the lumbar spine or adjacent to the pump (e.g., in the abdomen or over the back). As described herein with other embodiments the device 100 may be coupled, during use, to an internal or an external pump. In the current embodiment, features described herein to prevent cross contamination (e.g., a barrier) may be utilized. In the current embodiment, features described herein may be utilized including wherein the ends of the lumens being separated by a distance (e.g., 5 mm to 1 cm). The container (e.g., sampling reservoir) may separate from the double lumens so that the lumens are joined but the container has been separated from the joint lumens. For example, a T-shaped separation may be used in the tubing with one pathway from the T moving towards an aspiration reservoir and one pathway towards the infusion system. A T coupling 115 may be used in other embodiments disclosed herein. An installation stylet as described herein may be temporarily positioned in the infusion lumen or the aspiration lumen during placement in a subject. The device may be positioned using neuroimaging or other forms of intraoperative detection. Markers (e.g., metal portions of the device) may be used for neuroimaging (e.g., CT or MRI). Markers (e.g., a magnetic piece) may be used for intraoperative detection.

In some embodiments, installing the access device 100 may include positioning the lumens in a burr hole above the cerebellum on the left or right side. FIG. 6 depicts a diagram of a cross sectional view of an embodiment of an access device 100 implanted with the sampling and infusion ports located adjacent, behind or over the cerebellum 208. The infusion and sampling catheter in the brain is connected to a container 120 which is in turn connected to an implantable pump that is located in the abdomen. In some embodiments, a small microinsertion device may be used to position the lumens of the device through a small opening of less than one centimeter such that the lumens go through the burr hole opening. The inserted lumens may be flat or shaped like a tubing with two different pathways in it. The infusion pathway may infuse durally towards the dura or towards the brainstem or medial or lateral. The aspiration pathway may positioned in an opposing direction to the infusion lumen, specifically such that the opening of the aspiration lumen is directed in an opposing direction to the opening of the infusion lumen. In some embodiments, the openings may be facing the same direction.

The pathway of placing the device may be determined by a CT scan or an MRI scan preoperatively. Scans may depict the subarachnoid cisterns and placement of the catheter in the cerebellum. The targets could be any of the CSF subarachnoid cisterns including the cisterna magna, supracerebellar cisterns, CPA cistern or anterior to the brain stem cisterns. In some embodiments, a T-shaped separation 115 of the tubing as described herein may include one pathway directed towards an aspiration reservoir and one pathway directed towards an infusion system. In some embodiments, a stylet as described herein may be placed in the infusion lumen (or the aspiration lumen) when positioning the device in the subject. This same approach could be used to position the device over the sylvian fissure or interhemispheric cistern.

Elements in common to both a supracerebellar device and a hemisphere design include positioning the lumens through a small opening. Other common elements may include using preoperative imaging as a positioning guide and potentially using intra operative imaging as a positioning guide using either magnetic pieces in the device to see location and shape or using intraoperative MRI or intraoperative CT scan during positioning of the device. Common elements may include having a shape so that it would be anchored to the skull outside the cranium, and/or a stylet to guide passageway. For example, the container may include exterior adhesive means for coupling the container to an exterior surface of the cranium.

Figure 7:
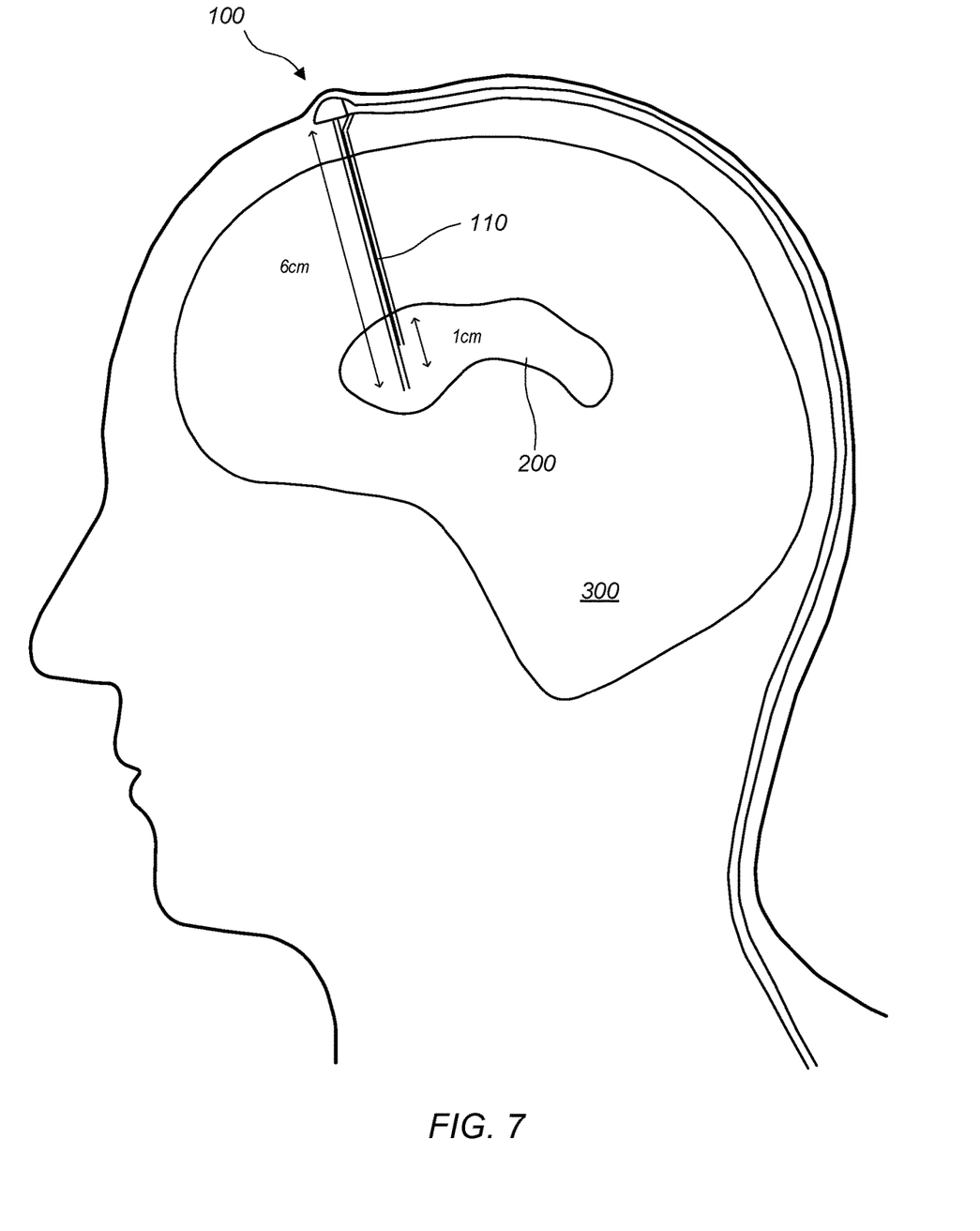
FIG. 7 depicts a diagram of a cross sectional view of an embodiment of a portion of an intraventricular access device, specifically a side by side dual lumen design. The infusion and sampling ports are implanted in one of the lateral ventricles. The infusion port (right lumen in illustrator) is connected to an implanted pump located near the abdomen.

In some embodiments, the aspiration lumen and the infusion lumen are different lengths when positioned, during use, in the subject's brain such that a distal end of the aspiration lumen and a distal end of the infusion lumen are positioned a distance away from one another. FIG. 7 depicts a diagram of a cross sectional view of an embodiment of a portion of an intraventricular access device 100, specifically a side by side dual lumen design. The infusion and sampling ports 110 are implanted in one of the lateral ventricles 200. The infusion port (110b) is connected to an implanted pump located near the abdomen. Positioning the distal ends of the aspiration and infusion lumens a distance away from one another may inhibit cross contamination of fluids.

Figures 8A, 8B, 8C:
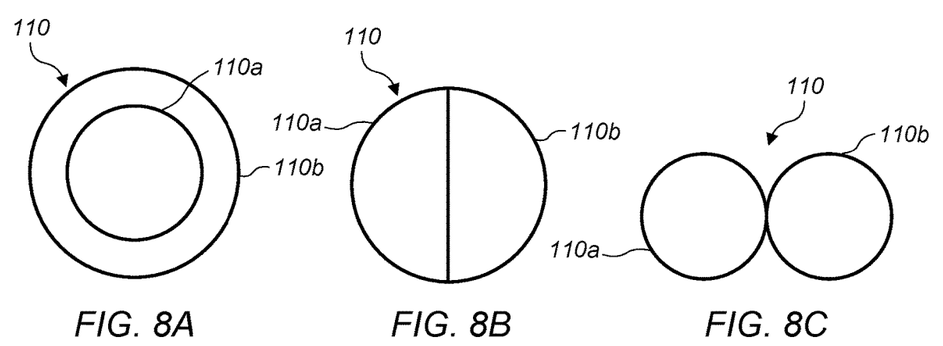
FIGS. 8A-F depict diagrams of a cross sectional view of several embodiments of a various dual lumen catheters that may be used for the device described herein as well as one or more stylets positioned in one or more of the lumens.

The aspiration and infusion lumens may have different physical relationships relative to one another. FIGS. 8A-C depict diagrams of a cross sectional view of several embodiments of a various dual lumen catheters 110 that may be used for the device described herein. In some embodiments, at least a portion of the infusion lumen is positioned in the aspiration lumen or at least a portion of the aspiration lumen is positioned in the infusion lumen (e.g., as depicted in FIGS. 1 and 8A). In some embodiments, the aspiration lumen and the infusion lumen may include a single lumen divided into two different lumens with a wall or divider (e.g., as depicted in FIG. 8B). In some embodiments, the aspiration lumen and the infusion lumen may include two different lumens positioned adjacent one another (e.g., as depicted in FIGS. 5 and 8C).

In some embodiments, a distal end of the aspiration lumen comprises a first opening and a distal end of the infusion lumen comprises a second opening. The first opening and the second opening may be directed in a substantially opposing directions (e.g., at least orthogonally relative to one another) to inhibit cross contamination of fluids. The openings may be directed away from one another by bending (e.g., during fabrication and/or implantation) at least a portion of at least one of the distal ends of the aspiration and/or infusion lumen.

Figure 9:
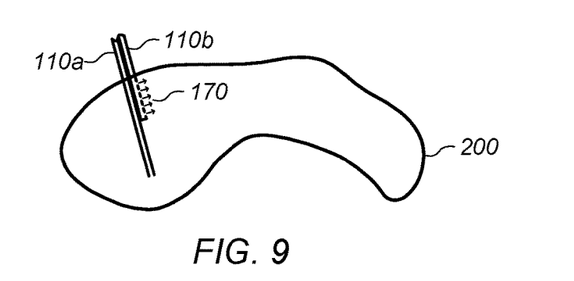
FIG. 9 depicts a diagram of a cross sectional view of an embodiment of a portion of an intraventricular access device, specifically a side by side dual lumen design with multiple flow holes in the infusion catheter. The flow holes may be open or may each consist of small "slits" that open when drug is infused (when there is positive pressure) and close when drug is not infused.

In some embodiments, a distal end of the aspiration lumen and/or the infusion lumen comprises at least one opening or a plurality of openings. In some embodiments, a distal end of the aspiration lumen and/or the infusion lumen comprises at least one opening which is inhibited from opening except when pressure is applied to the opening. FIG. 9 depicts a diagram of a cross sectional view of an embodiment of a portion of an intraventricular access device 100, specifically a side by side dual lumen design with multiple flow holes 170 in the infusion catheter 110b. The flow holes may be open or may each consist of small "slits" that open when drug is infused (when there is positive pressure) and close when drug is not infused. This may be accomplished using a number of different methods. For example the opening may include a slit cut into a substantially resilient materials which flexes when under pressure but returns to an original shape after the pressure subsides (the original shape being a substantially closed slit in the lumen). The opening may include a more traditional opening closed off with a hinged cover (e.g., the hinge may include a resilient material as described herein since traditional mechanical hinges may be difficult to manufacture at the current dimensions).

In some embodiments, at least a portion of the container is formed from material that is penetrable by a needle and substantially reseals after extraction of the needle. In some embodiments, specialized needles may be employed that allow resealing and multiple penetrations when cerebrospinal fluid is aspirated. Specialized needles may include non-coring needles. For example a small non-coring butterfly needle may be used to (e.g., 23 or 25 gauge connected to a three-way tap) access the reservoir and collect a small amount of CSF.

The portion of the container may be on a proximal portion at least in a relation to the aspiration lumen such that the portion is facing away from the subject and therefore accessible. At least a portion or all of the container may be positioned subcutaneously in the subject (e.g., between a subject's skull and skin). The resealable portion of the container may be exposed through the skin of the patient or be positioned beneath the skin. The resealable portion of the container may be formed from silicon. The reasealable portion may include an opening with a recloseable cap or stopper. The resealable portion may be replaceable after implantation.

Up to 25% of brain catheters fail due to clotting or tissues growing into the catheter holes. Thus, there is a need for a new type of catheter to limit tissue adherence as well as the risk of infection. Fibrous adhesions may bind the intrabrain portion of the infusion system to the proximate choroid plexus. Gentle rotation may free the catheter from the choroid plexus. If the catheter is stuck to the choroid plexus and is forcefully removed, there may be intraventricular hemorrhage. Thus, there exists a need to develop a catheter with an outer coating that also limits adherence and in-growth of tissue, particularly from the choroid plexus. In some embodiments, at least portions of the device are formed from and/or coated in biocompatible materials which inhibit cell adhesion. In some embodiments, biocompatible materials such as Pebax, HDPE, LDPE, PTFE (polytetrafluoroethylene), ePTFE (expanded polytetrafluoroethylene), and polyimide may be used to inhibit cell adhesion. For example, as regards ePTFE independent experimental and clinical studies have demonstrated that the tight microstructure of the ePTFE surface of GORE PRECLUDE® PDX Dura Substitute is effective at minimizing tissue attachment. With an average porosity of less than one micron, the microstructure prevents penetration by fibroblasts and other mesenchymal cells and thus minimizes dense fibrous ingrowth.

In some embodiments, mechanical smoothing may be used on portions to limit micro locations for adhesions and the shapes of the holes can be made slit-like or very small via manufacturing techniques such as laser micromachining.

In some embodiments, at least portions of the device are formed from and/or coated in biocompatible materials comprising an antimicrobial. Antibacterial coatings composed of either silver or antibiotic impregnation similar to the catheters currently on the market. Portions of the device may be impregnated with antibiotics (e.g., rifampicin and clindamycin).

Choice of materials may be important as regards manufacture of devices described herein. For example, granuloma associated with morphine spine infusion has been of concern. Being careful of the molecule (morphine appears to be a major culprit), making sure the device materials in the infusion system are produced using high quality products to avoid impurities, and/or placing the catheter in areas of high CSF flow relative the flow in the spinal areas, may result in the risk for granulomas being minimized.

The system can either be modular or in one continuous system. The catheter is in one system or can be in two pieces from the container. The container may be either preassembled with a top or with the top that can be added separately. If the top is in place, a modified spinal needle or another rigid type device is necessary for controlled placement. If it is in two pieces a standard cannula can be in place that is not sharp.

In some embodiments, during implantation general procedures of import may include long tunneling, antibiotic cuffs at entry sites, using filters, avoiding flushing, maintaining sterile techniques, sometimes using injected antibiotics and/or educating patients on self-care.

Figure 10:
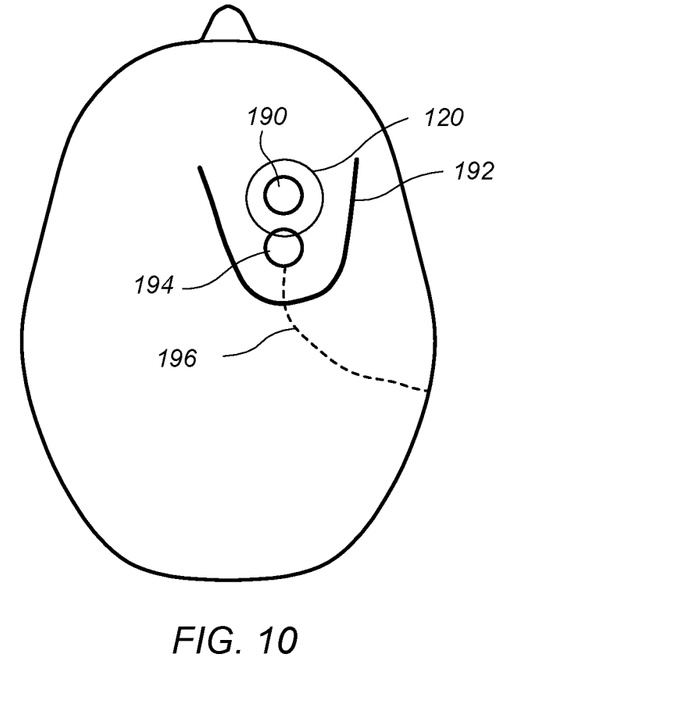
FIG. 10 depicts a diagram of a top view of an embodiment of a portion of an implanted intraventricular access device detailing an implantation method.
Figure 11:
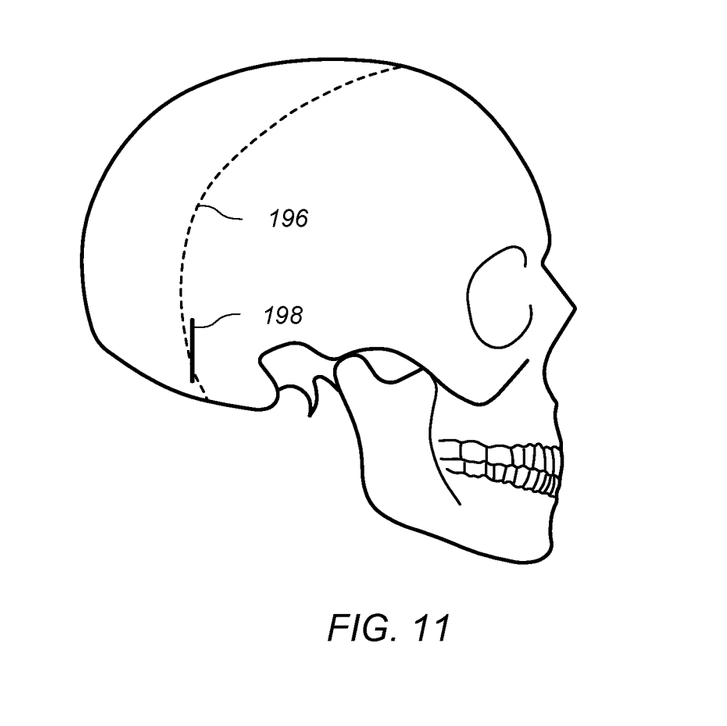
FIG. 11 depicts a diagram of a side view of an embodiment of a portion of an implanted intraventricular access device detailing an implantation method.
Figure 12:
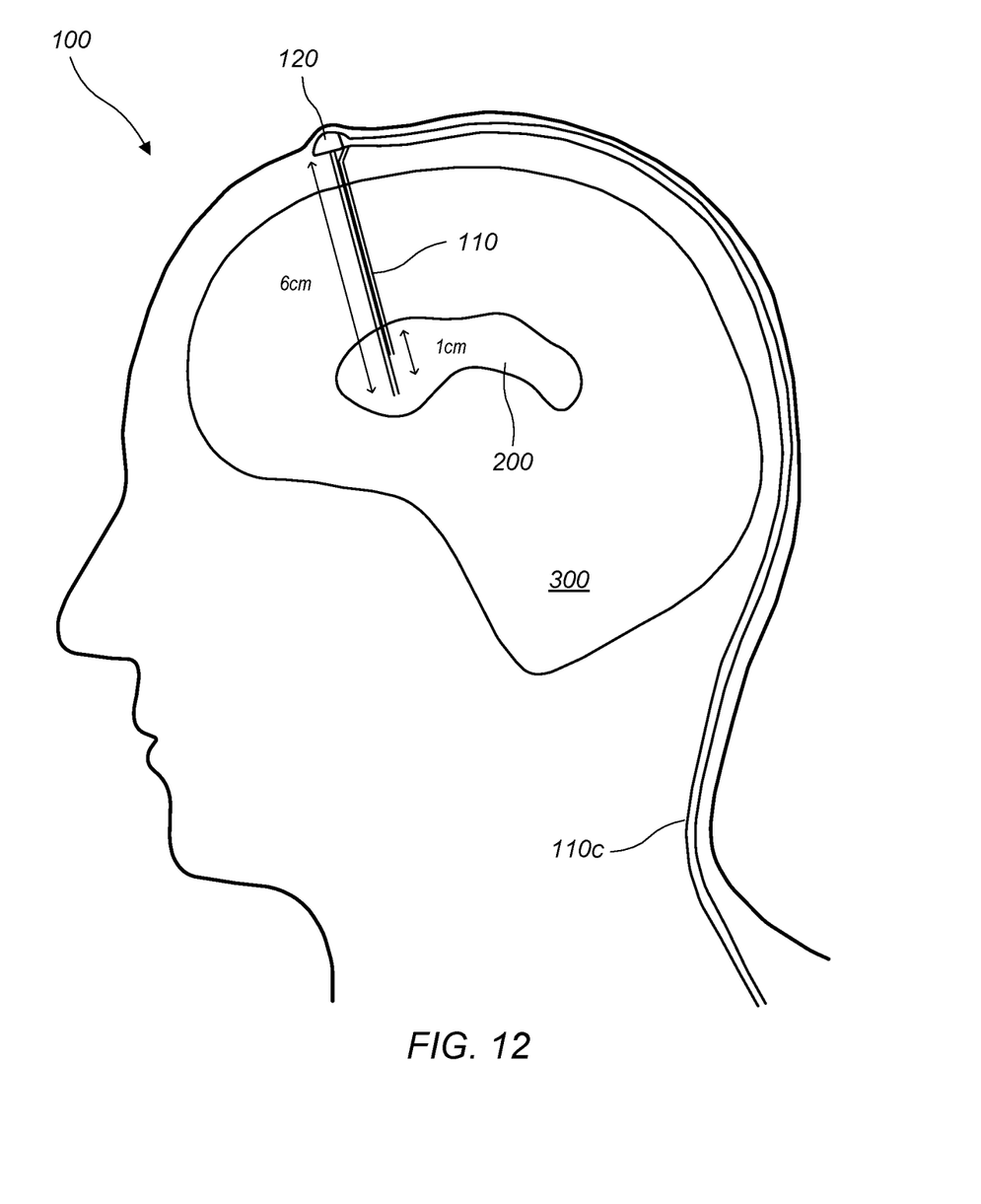
FIG. 12 depicts a diagram of a cross sectional view of an embodiment of a portion of an implanted intraventricular access device detailing an implantation method.

FIGS. 9-11 depicts a diagram of a top view of an embodiment of a portion of an implanted intraventricular access device detailing an implantation method. In some embodiments, insertion of devices described herein may include inserting extraventricular drains at Kocher's point 190, to have the catheter tip in the frontal horn of the lateral ventricle. The catheter may be inserted on the right side of the brain via a frontal incision 192. The burr hole 194 may be created using a ventriculostomy procedure, sterile techniques, verification of catheter placement, tunneling 196 (including one or more incisions 198) and connections to drug pump. The catheter is designed to facilitate ease of use, accuracy, safety and durability of the procedure and the implant.

In some embodiments, a method includes aspirating and infusing at least a portion of a subject's brain fluid. The method may include penetrating an upper portion of a container of a device using a needle. The method may include aspirating a first fluid from a first portion of a subject's brain fluid through an aspiration lumen coupled to the container and using the needle. The method may include infusing a second fluid into a second portion of a subject's brain fluid through an infusion lumen coupled to the container and the aspiration lumen. The method may include inhibiting penetration of the infusion lumen by the needle.

In some embodiments, the method may include infusing the second fluid using a pump coupled to the infusion lumen. The pump may be positioned externally or internally (e.g., subcutaneously, in a body cavity, etc.) relative to the subject. The method may include positioning at least a portion of the infusion lumen coupled to a pump subcutaneously.

Figures 8D, 8E, 8F:
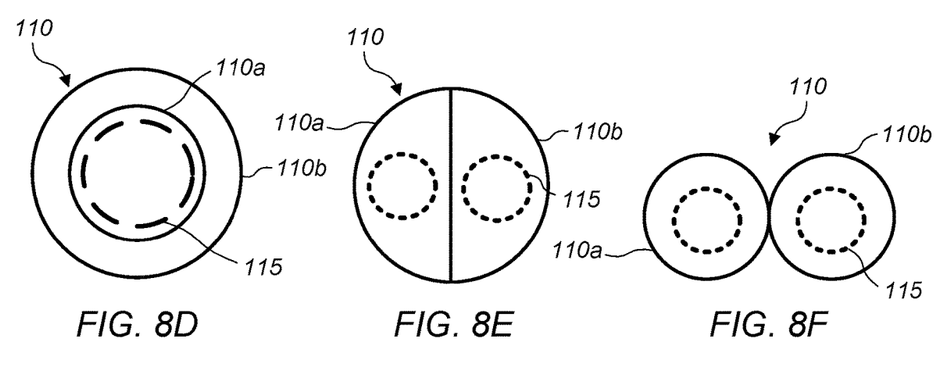

In some embodiments, the method may include positioning at least a portion of the aspiration and/or the infusion lumen in the subject's brain using a substantially inflexible stylet. The stylet may be positioned in the aspiration lumen by running the stylet through the container. FIGS. 8D-F depict a stylet 115 positioned in one or more lumens during installation of the device described herein. The stylet 115 may be used to insert the device in a subject's brain fluid. The stylet may be positioned in the aspiration and/or the infusion lumen. The stylet may be more than about 7 cms in length. The stylet may penetrate at least ½ the length of the aspiration catheter within the brain during use. If the stylet is positioned in both lumens, either two stylets may be used or one stylet with a split end may be used. The method may include observing at least a portion of the device during implantation using neuroimaging (e.g., MRI). Towards that end many if not all of the materials used to form the device may be compatible with common neuroimaging devices such as MRI.

In some embodiments, a stylet may be used to assist insertion of the device by positioning the stylet in the aspiration lumen before the reservoir or through the reservoir for aspiration. In some embodiments, a stylet may be used to assist insertion of the device by positioning the stylet in the infusion lumen before connection to an implantable or external pump.

In some embodiments, the method may include inhibiting penetration of the infusion lumen by the needle using a barrier positioned between a proximal opening of the aspiration lumen and at least a portion of the infusion lumen adjacent to and/or associated with the container. The barrier may inhibit cross contamination in general between the lumens. In some embodiments, the barrier may be formed from the same materials as the container but may consist of a greater thickness (this may tactically alert a care giver inserting a needle that they are unknowingly inserting the needle to far into the container and close to penetrating the barrier. In some embodiments, the barrier may be formed from a different material than the container. The barrier may be formed from a substantially rigid, rigid, or inflexible material such as PTFE or a metal or metal composite.

In some embodiments, the method may include inhibiting at least one opening at a distal end of the aspiration lumen and/or the infusion lumen from allowing fluids through the opening except when at least predetermined amount of pressure is applied to the opening in a first direction. The method may include inhibiting the opening from allowing fluids through the opening in a second direction even under pressure.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of aspirating and infusing into a subject's cerebrospinal fluid, comprising:
    penetrating an upper portion of an implanted container using a needle,
        wherein the container is coupled to a catheter,
        wherein the catheter comprises an aspiration lumen, an aspiration opening in fluid communication with the aspiration lumen, an infusion lumen, and an infusion opening in fluid communication with the infusion lumen,
        wherein the aspiration lumen and the infusion lumen are fluidically isolated from one another,
        wherein the container comprises (i) an infusion pathway in communication with the infusion lumen, and (ii) a sampling port in communication with the aspiration lumen, wherein penetrating the upper portion of the container with the needle causes the needle to be placed in the sampling port, wherein the sampling port comprises a cone-shaped guide configured and arranged to position the needle relative to the aspiration lumen, wherein the guide serves as a barrier to inhibit penetration of the needle into the infusion pathway;
    aspirating the subject's cerebrospinal fluid through the aspiration opening, the aspiration lumen, and the sampling port using the needle;
    infusing a therapeutic fluid into the subject's cerebrospinal fluid through the infusion pathway, the infusion lumen and the infusion opening.

2. The method of claim 1, further comprising inhibiting opening of the aspiration opening except when pressure is applied to the aspiration opening and/or inhibiting opening of the infusion opening except when pressure is applied to the infusion opening.

3. The method of claim 1, wherein opening of the aspiration opening is inhibited except when pressure is applied to the aspiration opening in a first direction.

4. The method of claim 1, wherein the aspiration lumen and the infusion lumen are parallel and adjacent to each other until they reach the container or alternatively for at least a portion of a length of the catheter.

5. The method of claim 4, wherein the aspiration lumen and the infusion lumen are integrated together and provide for side-by-side flow.

6. The method of claim 5, wherein the aspiration lumen and the infusion lumen are circular in cross-section.

7. The method of claim 6, wherein the aspiration lumen and the infusion lumen are each individually circular in cross-section.

8. The method of claim 1, wherein at least a portion of the infusion lumen is positioned in the aspiration lumen or at least a portion of the aspiration lumen is positioned in the infusion lumen.

9. The method of claim 1, wherein the aspiration lumen and the infusion lumen comprise two different lumens positioned adjacent and coupled to one another.

10. The method of claim 1, wherein the aspiration lumen and the infusion lumen are different lengths and have different tip locations when positioned, during use, in the subject's cerebrospinal fluid such that a distal end of the aspiration lumen and a distal end of the infusion lumen are positioned a distance away from one another.

11. The method of claim 1, wherein a distal end of the aspiration lumen comprises the aspiration opening and a distal end of the infusion lumen comprises the infusion opening, and wherein the aspiration opening and the infusion opening are directed in substantially opposing directions to inhibit cross contamination of fluids.

12. The method of claim 1, wherein at least a portion of the container is formed from a material that is penetrable by the needle and substantially reseals after extraction of the needle.

13. The method of claim 1, wherein the container comprises a marker to indicate a position of the barrier and/or the center of the container to target aspiration.

14. The method of claim 1, wherein at least a portion of the catheter is formed from and/or coated in biocompatible materials which inhibit cell adhesion and/or comprises an antimicrobial.

15. The method of claim 1, wherein the container is located beneath a scalp of the subject.

16. The method of claim 15, wherein the container is located outside a skull of the subject.

17. The method of claim 1, wherein the infusion lumen is fluidically connected to a pump positioned externally or internally relative to the subject, wherein the infusing is performed by the pump.

18. The method of claim 17, wherein the pump is located in a torso of the subject.

19. The method of claim 17, wherein the pump is located in an abdomen of the subject.

20. The method of claim 1, wherein at least a portion of the aspiration lumen and the infusion lumen are located in a spinal canal of the subject.

21. The method of claim 1, further comprising positioning the catheter partially in or adjacent to a brain or spinal cord of the subject, wherein the positioning is performed before the penetrating.

22. The method of claim 1, wherein the aspiration opening and the infusion opening are separated by a distance from 5 mm to 1 cm.

23. The method of claim 1, wherein the aspiration opening and the infusion opening are separated by a distance along a length of the catheter, wherein the aspiration opening is positioned in a first portion of the subject's cerebrospinal fluid, and wherein the infusion opening is positioned in a second portion of the subject's cerebrospinal fluid.

* * * * *